United States Patent [19]

Furihata

[11] 3,958,566
[45] May 25, 1976

[54] SUCTION CONTROL DEVICE FOR AN ENDOSCOPE

[75] Inventor: Hiroyuki Furihata, Tokyo, Japan

[73] Assignee: Olympus Optical Co., Ltd., Tokyo, Japan

[22] Filed: Aug. 23, 1974

[21] Appl. No.: 500,162

[30] Foreign Application Priority Data
Aug. 27, 1973  Japan.......................... 48-100395[U]
Sept. 25, 1973  Japan.......................... 48-111592[U]

[52] U.S. Cl. .................................... 128/4; 128/2 F; 128/274; 128/276; 137/604; 137/625.68
[51] Int. Cl.²........................................... A61B 1/00
[58] Field of Search.... 128/240, 247, 274, 276–278, 128/4–11, 2 B, 2 F, 349 BV; 137/604, 625.68

[56] References Cited
UNITED STATES PATENTS
3,517,669   3/1968   Buono et al. ........................ 128/276
3,830,225   8/1974   Shinnick............................. 128/2 B

*Primary Examiner*—Robert W. Michell
*Assistant Examiner*—Henry S. Layton

[57] ABSTRACT

A sliding tube is disposed within a cylindrical insertion pipe. Around the insertion pipe there is provided a surrounding wall member defining a space with the pipe, said space communicating with a suction instrument via a suction pipe and simultaneously with the interior hole of the insertion pipe via a communicating port. The opening planes of the respective upper end opening portions of the insertion pipe and space are rendered substantially flush with each other, each of said upper end opening portions having a size large enough to permit it to be closed by the operator's finger. When an injection instrument is fitted into the upper end opening of the insertion pipe, the sliding tube is lowered to close said communicating port. The surrounding wall member is detachably fitted to a receiving member secured to an endoscope body.

9 Claims, 12 Drawing Figures

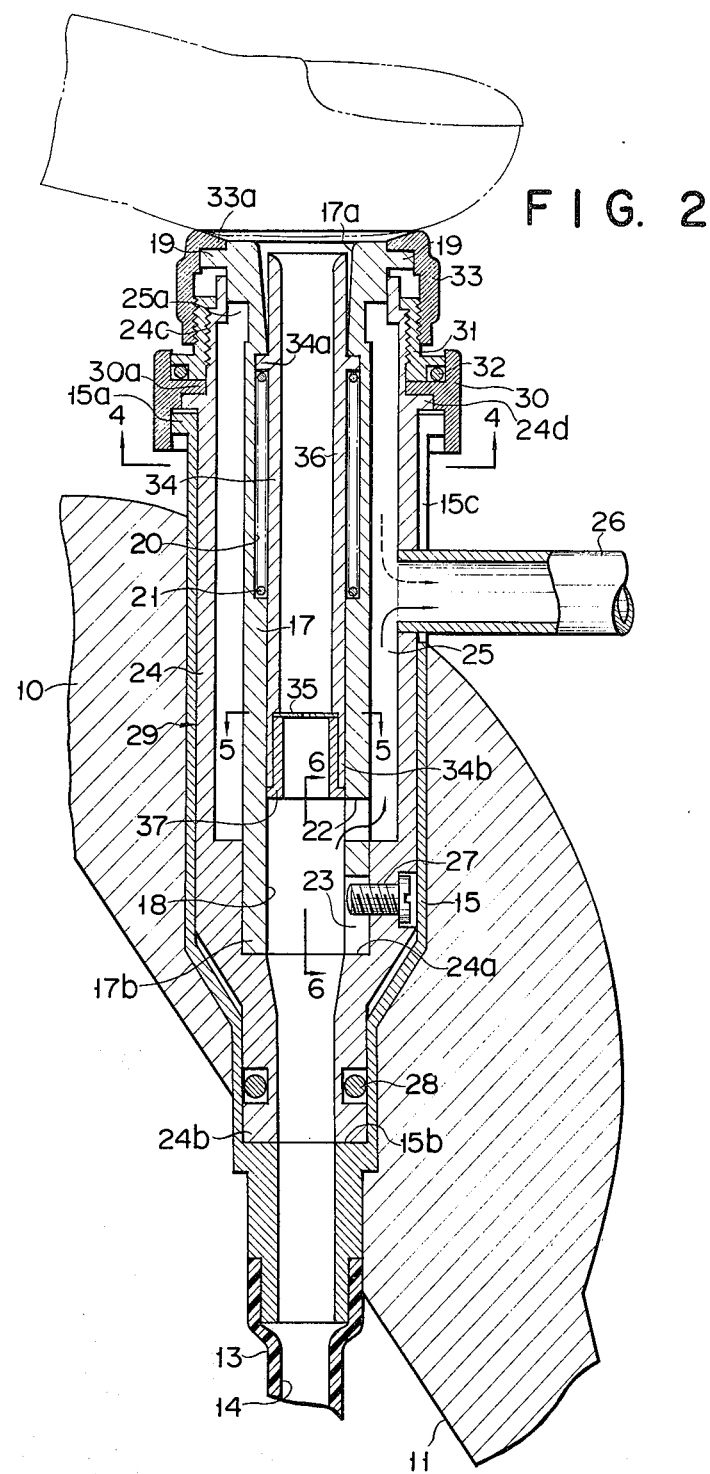

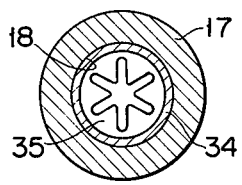
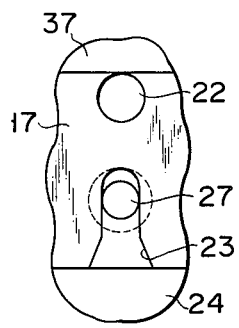
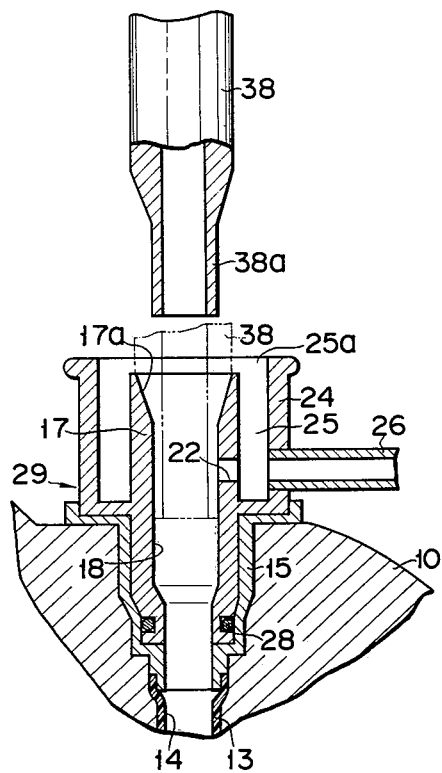
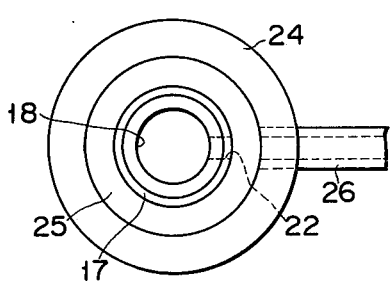

SUCTION CONTROL DEVICE FOR AN ENDOSCOPE

BACKGROUND OF THE INVENTION

This invention relates to a suction control device for an endoscope mounted on the endoscope body for sucking, for example, a body liquid or filth in the body cavity of a human being via a channel formed in the endoscope body, thereby to discharge it to the exterior, and for sending a medical treatment fluid such as a stupefacient or contrast material into the body cavity via said channel, by being fitted with the tip end portion of an injection instrument such as a syringe.

Where, in observing the interior of the body cavity utilizing the endoscope, a body liquid, filth or expectoration are present at the affected part of the body cavity, they constitute an obstacle to the observation and simultaneously blur the view field objective lens of the endoscope. Accordingly, it is required to remove such obstacle by operating the aforesaid suction control device. Furthermore, when it is desired to observe a digestive organ, it becomes necessary to eliminate superfluous air therefrom, and for deaerating the organ the suction control device is used.

The conventional suction control device comprises an outer tube connected to a suction instrument via a suction pipe, an inner tube slidably disposed within the outer tube and normally raised up to a normal position by the biasing force of a spring, an insertion pipe provided separately from said outer tube so as to communicate with the channel of the endoscope body, to permit, for example, a forceps to be inserted into the channel from the upper end opening portion of said pipe, and enable a medical treatment fluid to be injected into the channel by fitting the tip end portion of an injection instrument to said opening portion, and a communicating port for allowing the insertion pipe to communicate with said outer tube. Said communicating port is generally so constructed that it is normally so closed by the inner tube as to fail to perform the communicating action. And in inserting, for example, a forceps, or injecting a medical treatment fluid, the communicating port remains closed to prevent the sucking action from reaching the channel. In this case, since air is sent into the suction device from the upper end opening portion of the inner tube, application of an excessive load to the suction instrument is prevented. On the contrary, in sucking, for example, a body liquid, the upper end opening portion of the insertion pipe is first closed by, for example, a rubber stopper and simultaneously the upper end opening portion of the inner tube is closed with the operator's finger, and the inner tube is then pushed down against the biasing force of the spring, whereby to open the communicating port. Since, at this time, the sucking action comes to reach the interior of the insertion pipe and, further, the channel via the communicating port, a body liquid, for example, within the body cavity is sucked into the suction pipe by being passed through the channel, insertion pipe, communicating port and outer tube.

As above described, in sucking, the closure by the rubber stopper of the upper end opening portion of the insertion pipe and the manual closure of the inner tube are required each time sucking is effected, so that the sucking operation becomes extremely troublesome.

Particularly, in the case of a bronchoscope observation among the endoscope observations, frequent sucking operations are required for removing an expectoration, blood having come out of the body organ or for preventing blurring the view field objective lens. Also very often a stupefacient has to be injected in order to cause the patient's cough to stop during said sucking operations by fitting the injection instrument into the opening portion of the insertion pipe over and over again as required or contrast material has to be injected for the purpose of taking an X-ray photograph of the bronchia. For the foregoing reasons, the construction wherein the insertion pipe is provided separately from the inner and outer tubes as in the construction of the prior art device renders it extremely difficult to permit the viewer or observer to carry out a quick operation and simultaneously produces the possibility of an erroneous operation. Further, in the case of the above mentioned bronchoscope observation, the operation delay has a bad influence on the patient's respiration function, which particularly requires a quick operation.

For the purpose of achieving the foregoing speediness of the operations as much as possible, the prior art device has been improved, for example, by forming the upper end opening portion of the insertion pipe into a shape permitting it to be readily fitted with an injection instrument such as a syringe, which however has not yet attained a sufficient effect.

On the other hand, where it is desired to achieve the speediness of the operations, the washing and disinfecting operations of the suction control device inevitably required before the device once used is again employed should be performed in a shorter time. Such device washing and disinfecting operations are required for preventing infection due to infective pathogenic bacteria, and generally are carried out with respect to the whole of the endoscope including the suction control device.

In the endoscope fitted with the prior art suction control device, however, the suction control device is assembled in a manner integral with the endoscope body and simultaneously is complicated in its construction, which fails to cause the suction control device to be washed and disinfected to a sufficient extent.

SUMMARY OF THE INVENTION

One feature of the suction control device according to the invention resides in the specific construction wherein a cylindrical surrounding wall member for at least partially surrounding the outer circumference of the insertion pipe and defining a space therewith is provided, to which a suction pipe is connected; and an opening means for allowing the interior of the insertion pipe to communicate with the space is provided, the upper end opening plane of the insertion pipe being made substantially flush with the upper end opening plane of the space.

This suction control device having the foregoing feature enables the respective upper end opening portions of the insertion pipe and the space to be closed at one time by the operator's finger, so that the suction operation can be quickly or speedily carried out, which eliminates the major drawbacks encountered with the prior art device.

Another feature of the suction control device according to the invention resides in that the body of the suction control device is detachably fitted to the endoscope body. To this end, a receiving member for being fitted with the wall member to receive the same therein is secured to the endoscope body, the space between the receiving member and the wall member being retained in a liquid tight condition by seal means. And under the condition where the suction control device is in use, the wall member is fitted into the receiving member and is separably locked to the fitted position by locking means.

This suction control device having such feature can be subjected to a satisfactory washing and disinfection by disconnecting the device body alone from the endoscope body and yet enables the washing and disinfecting operations to be speedily performed in safety.

In one embodiment of the suction control device of the invention, the space between the insertion pipe and the wall member is provided concentrically with respect to the longitudinal axis of the insertion pipe. Accordingly, the device as a whole can be made compact and for closing the respective opening portions of the space and the insertion pipe with the operator's finger can more easily be carried out.

Within the insertion pipe there is disposed a sliding tube urged by the spring so as to be normally held in a raised position, and said sliding tube is lowered upon fitting of the injection instrument into the upper end opening portion of the insertion pipe, thereby to close the opening means. Accordingly, when a medical treatment fluid such as a stupefacient or contrast material is sent into the channel by the injection instrument, the sucking action of the suction device on the channel is automatically stopped to enable the entry of the treatment fluid to be speedily or quickly conducted with high efficiency.

Further, in order that the suction control device may be more effectively washed and disinfected, the insertion pipe is rendered detachable from the wall member, and is separably fixed at the fitted position by a fixing ring.

In another embodiment of the invention, the arrangement is such that when the injection instrument is fitted into the upper end opening portion of the insertion pipe, the opening means is closed directly by the tip end portion of said instrument. For this reason, the tip end portion of the instrument is somewhat deeply inserted into the insertion pipe, the outer circumference of said tip end portion being exactly fitted to the inner wall of the insertion pipe. The foregoing construction simplifies the device structure without deteriorating the device function.

Accordingly, a primary object of the invention is to provide a suction control device for an endoscope which enables the sucking or injection operation to be quickly or speedily performed.

Another object of the invention is to provide a compact suction control device for an endoscope which is easily subjected to washing and disinfection by rendering the device body alone detachable from the endoscope body.

Other objects and advantages will become apparent from the content of hereinafter described embodiments and the content of the appended drawings.

BRIEF DESCRIPTION OF THE DRAWINGS

FIG. 2 is a longitudinal sectional view of a first embodiment of the suction control device of the invention;

FIG. 5 is an enlarged cross sectional view taken along line 5—5 of FIG. 2;

FIG. 6 is a fragmental view taken along line 6—6 of FIG. 2;

FIG. 8 is a longitudinal sectional view of a second embodiment of the suction control device of the invention;

FIG. 9 is an enlarged top surface view of FIG. 8;

DESCRIPTION OF THE PREFERRED EMBODIMENTS

Figures 1, 3, 4:
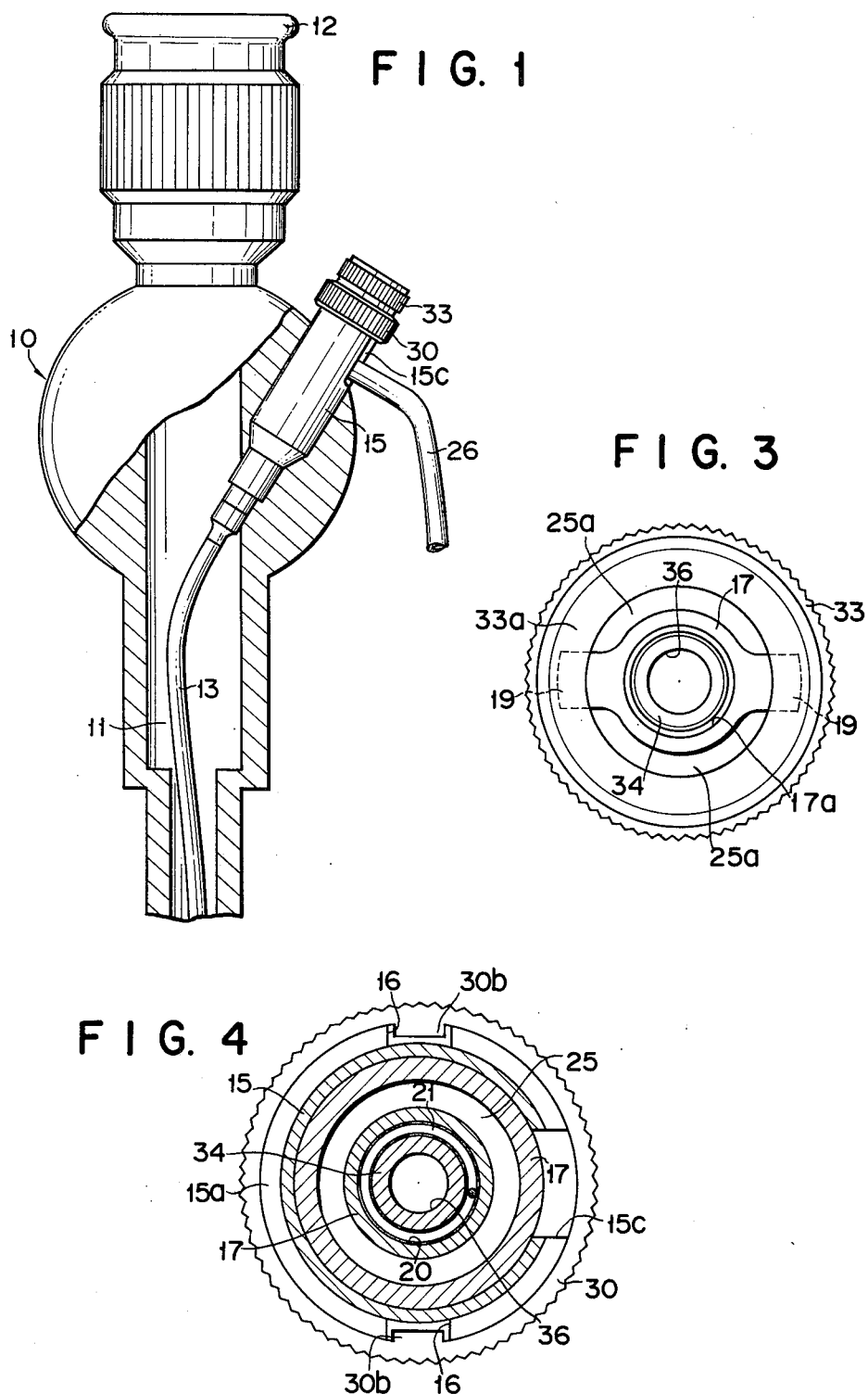
FIG. 1 is a side view, partly in section, of the base end section of an endoscope fitted with a suction control device of the invention.
FIG. 3 is an enlarged top surface view of FIG. 2.
FIG. 4 is an enlarged cross sectional view taken along line 4—4 of FIG. 2.

Referring to FIG. 1, only the base end section of an endoscope body 10 is shown, while the distal end section thereof which is to be inserted into a human body cavity being observed is not shown. Further, in FIG. 1, the flexible tube section of the endoscope body 10 connecting the distal end section to the base end section is partially shown. The endoscope body 10 itself has a conventional construction, namely, is formed interiorly with a main channel 11 for allowing the passage therethrough of an image guide fiber bundle or light guide fiber bundle and provided at the base end with an eyepiece portion 12. The viewer or operator performs various operations while viewing the eyepiece portion 12.

As shown in FIG. 1, the endoscope body 10 has attached thereto a suction control device according to the invention. The device is connected to a tube 13 extended into the main channel 11. The tube 13, as shown in FIG. 2, has an interior channel 14 for permitting the insertion or, for example, a forceps therethrough. The tube 13 is extended up to the distal end section not shown.

The structure of the suction control device will hereinafter be described by reference to FIG. 2.

To the endoscope body 10 is secured a cylindrical receiving member 15, the lower end portion of which is connected to the end portion of the tube 13 and formed with a hole (not numbered) communicating with the channel 14 within the tube 13. The receiving member 15 is provided at the upper end edge with a radially outwardly projecting flange 15a, and at the lower inner wall with a circumferential stepped portion 15b, and is further provided with a slit 15c having a desired width in a manner extending from the upper end thereof in the direction of the axial line thereof. Said flange 15a is formed with a pair of notches 16 diametrically facing each other as seen from FIG. 4.

A cylindrical insertion pipe 17 has a through bore 18 extending in the axial direction thereof, said through bore 18 being open both at the upper end and at the lower end. The inner wall surface of the through bore 18 at the upper end opening portion 17a of the insertion pipe 17 is so formed as to have an upwardly somewhat flaring tapered surface, which is suited for allowing the tip end portion of an injection instrument such as a syringe to be exactly fitted thereto as later described. The insertion pipe 17 is provided at the upper end portion with a pair of engagement projections 19 which project radially outwardly and diametrically face each other. The insertion pipe 17 has at its inner circumferential surface an axial annular recess 20, said recess 20 receiving a coil spring 21. Further the lower end portion 17b of the insertion pipe 17 is provided at one side with a communicating port 22 constituting opening means and a rotation preventing cut-out 23 for preventing the pipe 17 from being rotated about its longitudinal axis.

A cylindrical wall member 24 surrounds the insertion pipe 17. Accordingly, between the wall member 24 and the insertion pipe 17 is created an annular space 25 concentrical to the pipe 17, said space 25 communicating with the through bore 18 via the communicating port 22. The opening plane of the upper end opening portion 25a of the space is made substantially flush with the opening plane of the upper end opening portion 17a of the through bore 18. The space 25 is divided at the upper end opening portion into two parts by said pair of engagement projections 19.

To one side surface of the wall member 24 is attached one end of a suction pipe 26, which communicates with the space 25. The other end of the suction pipe 26 is connected to a suction instrument (not shown). The surrounding wall member 24 is provided at its lower inner wall with a circumferential stepped portion 24a, to which is detachably fitted the lower end portion 17b of the insertion pipe 17. In the fitted condition, the through bore 18 communicates with the channel 14 of the tube 13 via a bore (not numbered) formed in the lower end portion 24b of the wall member 24 and another bore (not numbered) formed in the lower end portion of the receiving member 15. Further, in the fitted condition, a screw 27 is screwed into the wall member in the proximity of its lower end and is engaged with the rotation preventing cut-out 23, preventing the insertion pipe 17 from being rotated relative to the wall member 24.

The surrounding wall member 24 is detachable from the receiving member 15, and the lower end portion 24b of the member 24 abuts against the stepped portion 15b of the receiving member. A seal ring 28 provides a liquid tight condition between the members 24 and 15. When the wall member 24 is fitted into the receiving member 15, the suction pipe 26 is entered into the slit 15c of the receiving member 15.

In this manner, the device body 29 including the wall member 24 and the insertion pipe 27 is rendered detachable from the receiving member 15, in other words, from the endoscope body 10.

The upper end portion of the cylindrical surrounding wall member 24 is provided at its outer circumference with a threaded portion 24c and a flange 24d. The flange 24d extends radially outwardly and engages the radially inwardly extending flange 30a of a locking ring 30. The locking ring 30, as shown in FIG. 4, is provided at the lower end edge with a pair of radially inwardly extending locking projections 30b diametrically facing each other, said projections 30b corresponding to said pair of notches 16 formed in the flange 15a. When, as shown in FIG. 4, this correspondence is maintained, the projections 30b may pass through the notches 16, so that locking between the members 15 and 24 is not achieved. When the ring 30 is rotated from the position of FIG. 4 in a clockwise or counter-clockwise direction, the projection 30b is engaged with the flange 15a, so that the receiving member 15 is locked to the wall member 24, so that the device body 29 is held in the fitted position within the receiving member 15. If, in case the body 29 is disconnected from the member 15, the locking ring 30 is rotated until the projection 30b comes to correspond to the notch 16, the body 29 may be pulled out readily in axial direction. It is to be noted here that the ring 30 is formed at the outer circumference with an anti-skid knurled portion so as to be easily rotatable manually by the operator.

A support ring 31 is fitted over the threaded portion 24c of the wall member 24 by screw engagement, and simultaneously urges the locking ring 30 downwardly via a ring-like spring 32. The ring 30 is prevented from being carelessly rotated by the action of this spring 32. Further, the support ring 31 is fitted into a fixing ring 33 by screw engagement. The fixing ring 33 is formed at the upper end edge with a radially inwardly extending flange 33a which engages the pair of engagement projections 19 of the insertion pipe 17. By fitting the fixing ring 33 over the support ring 31 by screw engagement, the flange 33a urges the projections 19 downwardly, so that the insertion pipe 17 is firmly fitted into the wall member 24. By releasing the screw engagement between the fixing ring 33 and support ring 31, the insertion pipe 17 can be pulled out from the member 24. It is to be noted that the outer circumference of the fixing ring 33 is also formed with an anti-skid knurled portion.

Within the insertion pipe 17 is disposed a sliding tube 34, the outer circumference of which is formed with a radially outwardly extending flange-like projection 34a which extends into said recess 20. The projection 34a is engaged by the upper end of the coil spring 21 which normally presses the projection 34a against the upper end of the recess 20 shown in FIG. 2. The sliding tube 34 is normally maintained in a raised position as shown in FIG. 2 by the spring 21. The tube 34, however, can be lowered from the raised position in an axially sliding manner against the spring 21, and the arrangement is such that when the sliding tube 34 is lowered, the lower end portion 34b thereof closes the communicating port 22. That is to say, the tube 34 functions to render ineffective the communicating action of the port 22 constituting opening means.

A rubber-made valve 35 is provided within the lower end portion 34b of the sliding tube 34 so as to close the interior hole thereof. The valve 35, as shown in FIG. 5, is formed with a plurality of slits extending radially outwardly from the center of the valve, said slits permitting the passage of a treating instrument such as a forceps or the passage of a stupefacient or contrast material forcibly flowed-in by an injection instrument but permitting little passage of, for example, a body liquid sucked out of the body cavity by a sucking appliance. Said valve 35 is fixed at the illustrated position by a pressing ring 37 fitted into the lower end portion 34b of the sliding tube 34.

The manner in which the suction control device having the foregoing construction is operated will now be described.

The endoscope is inserted into the body cavity of a human being or patient which is to be observed and the operator or viewer observes the affected portion of the body cavity through the endoscope while viewing the eyepiece portion 12. Simultaneously, the operator operates the suction control device. Where obstacles such as a body liquid, filth or expectoration are present at the affected portion of the body cavity, they have to be removed by the sucking operation.

With a suction instrument (not shown) operated, the operator, as shown in a two dots-dash line in FIG. 2, places his finger on the upper end of the suction control device, i.e., both on the upper end opening portion 17a of the insertion pipe 17 and on the upper end opening portion 25a of the space 25, thereby closing both opening portions 17a and 25a. Since both opening portions 17a and 25a are disposed concentrically to each other, they can be fully closed with the finger. Furthermore, since the arrangement is so that the opening planes of both opening portions 17a and 25a are rendered substantially flush with each other, the opening portions 17a and 25a can easily be closed with the finger.

Upon closure of both opening portions 17a and 25a, the sucking action reaches the channel 14 from the suction pipe 26 via the space 25, communicating port 22 and through bore 18, so that, for example, a body liquid within the body cavity is introduced into the channel 14, sent into the suction control device, and then flows into the suction pipe 26. When such body liquid is sent with force into the suction control device, it is liable to escape upwardly through the interior bore 36 of the sliding tube 34. Since, however, the valve 35 prevents such escape of the liquid, the liquid smoothly flows from the through bore 18 to the space 25 via the communicating port 22.

Figure 7:
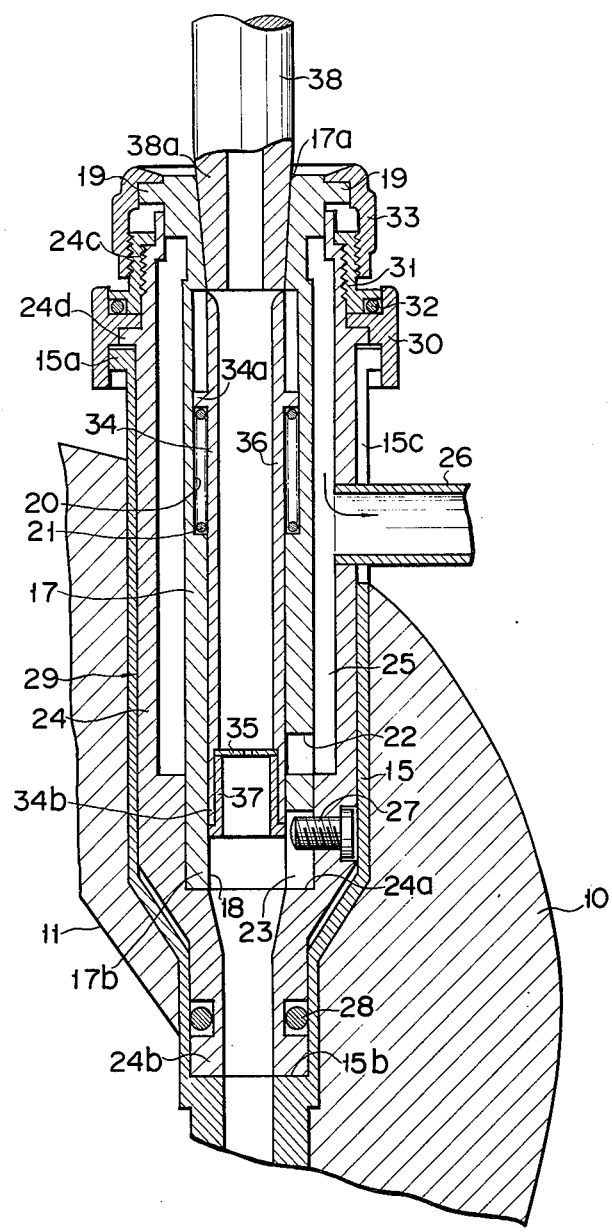
FIG. 7 is a longitudinal sectional view of the suction control device of FIG. 2, illustrating the condition in which the tip end portion of an injection instrument is inserted into the upper end opening portion of an insertion pipe.

Upon releasing the closure of both opening portions 17a and 25a, the sucking action substantially ceases to reach the channel 14. And the suction flow, as shown by a broken line of FIG. 2, is directed to the suction pipe 26 from the upper end opening portion 25a. This is because the opening area of the upper end opening portion 25a is made larger than the flowing area of the channel 14. In this case, it is to be noted that another suction flow from the upper end opening portion 17a of the insertion pipe 17 to the suction pipe 26 via the valve 35, communicating port 22 and space 25 is effected.

Where a medical treatment fluid such as an anesthesia agent or contrast material is sent into the body cavity through the channel 14, the tip end portion 38a of an injection instrument 38 for forcibly sending the fluid out is fitted into the upper end opening portion 17a of the insertion pipe 17, as shown in FIG. 7. At this time, the sliding tube 34 is pushed downwardly by the injection instrument 38, and as a result is lowered from the raised position against the biasing force of the spring 21, thereby automatically closing the communicating port 22 with the lower end portion 34b of the sliding tube 34. For this reason, the sucking action comes to have no effect on the through bore 18 and channel 14. As a result, the suction flows are reduced in number to a single flow directed from the upper end opening portion 25a of the space 25 to the suction pipe 26 as indicated by a solid line of FIG. 7. The presence of said single flow prevents an excessive load from being applied to the suction instrument (not shown) even when the communicating port 22 is closed.

The tip end portion 38a of the injection instrument 38 is formed into a tapered configuration, and the upper end opening portion 17a of the insertion pipe 17 is formed into a shape conformed with said tapered configuration. Accordingly, the injection instrument 38 is exactly fitted into the opening portion 17a. Accordingly, it is possible to forcibly send a desired fluid into the body cavity from the injection instrument 38 via the interior bore 36 of the sliding tube 34, through bore 18 and channel 14. Since, in this manner, the communicating port 22 is automatically closed by the action of the sliding tube 34 in response to the fitting operation of the injection instrument 38, the sucking or injection operation is simplified.

When the injection instrument 38 is withdrawn from the upper end opening portion 17a, the sliding tube 34 is returned again to the raised position by the biasing force of the spring 21, thereby to open the communicating port 22.

A treatment instrument such as a forceps other than the previously mentioned injection instrument 38 can of course be inserted into the channel 14 from the upper end opening portion 17a of the insertion pipe 17. Where said treatment instrument is inserted, it is not particularly necessary to close the communicating port 22 utilizing the lowering operation of the sliding tube 34.

In FIGS. 8 and 9, a second embodiment of the suction control device of the invention is shown. This embodiment will hereinafter be described with the parts and sections thereof associated with those of the first embodiment denoted by the same reference numerals.

In this embodiment, the sliding tube 34 of the first embodiment is not provided within the cylindrical insertion pipe 17. The aforesaid action of the sliding tube, i.e., the action that it automatically closes the communicating port 22 in response to the fitting operation of the injection instrument 38 is achieved by the tip end portion 38a of the instrument 38. In this embodiment, as indicated by a two dots-dash line of FIG. 8, the tip end portion 38a of the instrument 38 is not only inserted into the upper end opening portion 17a of the insertion pipe 17 but also is further inserted deeply into the through bore 18, thereby directly closing the communicating port 22 constituting opening means formed at the side wall of the insertion pipe 17 so as to permit the through bore 18 to communicate with the space 25 annularly provided around the insertion tube 17.

That is to say; by forming the tip end portion 38a of the injection instrument 38 so as to cause it to have a slightly larger length and forming the through bore 18 so as to cause it to have a length conforming with the length of the elongated tip end portion 38a, the injection instrument 38 itself is permitted to render ineffective the communicating action of the communicating port 22 through being fitted into the through bore 18. Therefore, the sliding tube becomes unnecessary.

In the second embodiment, the cylindrical surrounding wall member 24 is formed integral with the insertion pipe 17, and the space 25 is defined between the member 24 and the pipe 17 concentrically with respect to the longitudinal axis of the pipe 17 as shown in FIG. 9. The upper end opening portion 17a of the insertion pipe is made substantially flush with the upper end opening portion 25a of the space 25, and yet both opening portions 17a and 25a are respectively so formed as to have a size permitting both to be readily closed by the operator's finger.

To one side of the wall member 24 is connected one end of the suction pipe 26, thereby causing the pipe 26 to communicate with the space 25. The other end (not shown) of the suction pipe 26 is connected to the sucking appliance (not shown). The device body 29 comprising the wall member 24 and the insertion pipe 17 is detachably received within the receiving member 15 secured to the endoscope body 10. The lower end portion 24b of the wall member 24 is provided with a seal ring 28 for causing a liquid tight condition to be attained between the members 24 and 15. The receiving member 15 is connected to one end of the tube 13 having the channel 14.

The position at which the injection instrument 38 is fitted into the insertion pipe 17 is determined by the engagement between the tapered surfaces of both the instrument 38 and the pipe 17.

Although in this embodiment, the locking means for locking the receiving member 15 into the device body 29 is not provided, provision of this means, however, is easy when viewed from the standpoint of design.

Figure 10:
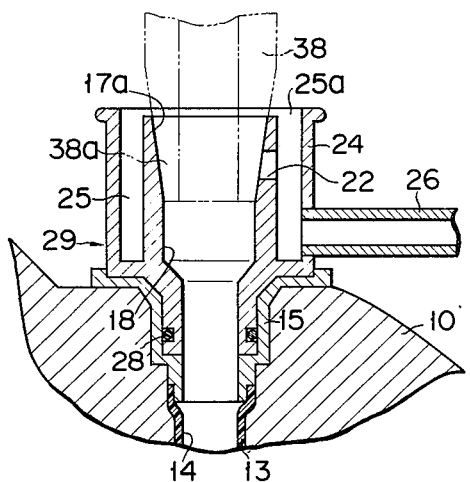
FIG. 10 is a longitudinal sectional view of a third embodiment of the suction control device of the invention.

In FIG. 10, a third embodiment of the suction control device of the invention is shown. This embodiment has a construction very similar to that of the second embodiment shown in FIGS. 8 and 9. The distinguishable point of this embodiment from the second embodiment resides in that the communicating port 22 is formed in the tapered upper end opening portion 17a of the insertion pipe 17. Accordingly, when the injection instrument 38 is fitted into the pipe 17, by causing the tapered surface of the tip end portion 38a of the instrument 38 to engage the tapered surface of the upper end opening portion 17a of the pipe as indicated by a two dots-dash line of FIG. 10, the instrument 38 is permitted to render ineffective the communicating action of the communicating port 22 constituting opening means. For this reason, the tip end portion 38a of the instrument 38 can do without being so formed as to have a particularly large length. Since the other constituent portions of this embodiment are the same as those of the second embodiment, they are only denoted by the same reference numerals and a description thereof is omitted.

Figure 11:
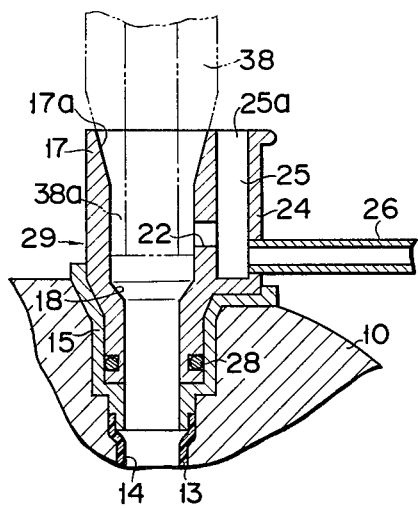
FIG. 11 is a longitudinal sectional view of a fourth embodiment of the suction control device of the invention.
Figure 12:
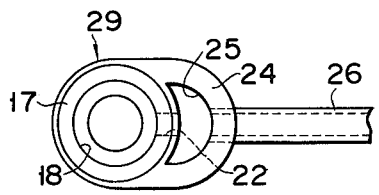
FIG. 12 is a top view of FIG. 11.

A fourth embodiment of the suction control device of the invention illustrated in FIGS. 11 and 12 is also similar in construction to the second embodiment of FIGS. 8 and 9. The distinguishable point of this embodiment from the second embodiment resides in that the space 25 between the cylindrical insertion pipe 17 and the wall member 24 is not annular but made crescent as shown in FIG. 12. Namely, the space 25 can not only be provided in a manner annular and concentrical to the insertion pipe so as to surround the whole outer circumference of the insertion pipe as in the preceding embodiments but also can be so formed as to at least partially cover the outer circumference of the pipe as in this embodiment. Accordingly this embodiment indicates the possibility of modifying such space 25. Also in the foregoing construction, the upper end opening portion 17a of the insertion pipe 17 is positioned flush with the upper end opening portion 25a of the space 25, both opening portions 17a and 25a being so formed as to have a size permitting them to be readily closed by the operator's finger.

Also in this embodiment, the tip end portion 38a of the instrument 38 is inserted from the upper end opening portion 17a of the pipe 17 deeply into the through bore 18, thereby closing the communicating port 22. Since the other constituent portions of this embodiment are the same as those of the second embodiment, they are only denoted by the same reference numerals and a description thereof is omitted.

As above described, the suction control device of the invention enables the sucking operation of, for example, a body liquid from the body cavity of a human being and the supply of a medical treatment fluid such as an anesthesia agent or contrast material through fitting the injection instrument into the insertion pipe, to be extremely readily performed, so that a quick and safe medical treatment can be carried out using the endoscope. Furthermore, where it is desired to subject the device to washing or disinfection, it can reliably be conducted because the device body is capable of being readily disconnected from the endoscope body.

What is claimed is:

1. A suction control device comprising: an endoscope having a body, a cylindrical insertion pipe having a through bore interiorly thereof and extending substantially in axial direction of said pipe, the lower end of said through bore communicating with a channel extending interiorly of said endoscope body and the upper end thereof being open to the exterior, said insertion pipe having an upper end opening portion with a shape permitting the end portion of an injection instrument to be inserted thereinto, a wall member surrounding at least partially the outer circumference of said insertion pipe and defining a closed space with said insertion pipe, a suction pipe, said space communicating with said suction pipe and having an upper end opening portion substantially flush with said upper end opening portion of said insertion pipe, and opening means formed in the insertion pipe for selectively establishing communication between said space and the through bore of said insertion pipe.

2. A suction control device according to claim 1, wherein said wall member surrounds the whole outer circumference of the insertion tube to cause the space to be disposed concentrically to the insertion pipe.

3. A suction control device according to claim 1, wherein said opening means comprises an opening closed by the end portion of an injection instrument when said instrument is inserted into said insertion pipe.

4. A suction control device according to claim 1, further comprising a cylindrical sliding tube slidably disposed within said insertion pipe substantially in axial direction thereof and when lowered from a raised position to close said opening means, a projection formed on the outer circumference of the sliding tube and projecting into an annular recess formed in the inner wall of the insertion pipe and extending substantially in axial direction thereof, and a spring received in said recess so as to normally hold the sliding tube in said raised position by engagement with said projection.

5. A suction control device according to claim 4, further comprising a valve provided within said sliding tube to substantially prevent the passage therethrough of a body liquid.

6. A suction control device according to claim 1, further comprising a cylindrical receiving member secured to the endoscope body, said wall member being separably engaged with said receiving member for mounting the wall member onto the endoscope body detachably therefrom, locking means for separably locking the wall member engaged with the receiving member, and sealing means located between the receiving member and the wall member.

7. A suction control device according to claim 6, wherein said locking means comprises a first flange projecting radially outwardly on the upper end edge of the receiving member and having at least one notch, a second flange projecting radially outwardly on the outer circumference of the wall member, and a locking ring having a third flange projecting radially inwardly so as to engage said second flange, and at least one radially inwardly extending projection corresponding to the notch of the first flange.

8. A suction control device according to claim 6, wherein said insertion pipe is detachable from the wall member, said wall member having a stepped portion for retaining the insertion pipe in a position in which the insertion pipe is fitted into the wall member, and fixing means for separably holding said insertion pipe in the fitted position.

9. A suction control device according to claim 8, wherein said fixing means comprises at least one projection projecting radially outwardly on the upper end of the insertion pipe, a fixing ring having a radially inwardly extending flange element engageable with said projection, and a support ring screwed to the outer circumference of the upper end portion of the wall member and screwed to said fixing ring.

* * * * *